(12) United States Patent
Goze et al.

(10) Patent No.: US 7,652,186 B2
(45) Date of Patent: Jan. 26, 2010

(54) METHOD OF MAKING LOW VISCOSITY PAO

(75) Inventors: Maria C. B. Goze, East Brunswick, NJ (US); Anatoly I. Kramer, Edison, NJ (US); Pramod J. Nandapurkar, Plainsboro, NJ (US); Norman Yang, Westfield, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 327 days.

(21) Appl. No.: 11/338,231

(22) Filed: Jan. 24, 2006

(65) Prior Publication Data

US 2006/0211904 A1 Sep. 21, 2006

Related U.S. Application Data

(60) Provisional application No. 60/662,728, filed on Mar. 17, 2005.

(51) Int. Cl.
*C07C 2/08* (2006.01)
(52) U.S. Cl. .................. 585/525; 585/520; 585/521
(58) Field of Classification Search .......... 585/520, 585/521, 525
See application file for complete search history.

(56) References Cited

U.S. PATENT DOCUMENTS

| 3,149,178 | A |   | 9/1964  | Hamilton et al. ........ 260/683.9 |
| 3,382,291 | A |   | 5/1968  | Brennan ............... 260/683.15 |
| 3,742,082 | A |   | 6/1973  | Brennan ............. 260/683.14 B |
| 3,780,128 | A |   | 12/1973 | Shubkin ................ 260/683.9 |
| 4,045,507 | A |   | 8/1977  | Cupples et al. ..... 260/683.15 B |
| 4,045,508 | A | * | 8/1977  | Cupples et al. ............. 585/511 |
| 4,172,855 | A |   | 10/1979 | Shubkin et al. ............... 585/16 |
| 4,956,122 | A |   | 9/1990  | Watts et al. |
| 5,693,598 | A |   | 12/1997 | Abraham et al. ........... 508/444 |
| 5,789,355 | A |   | 8/1998  | Adams et al. ............... 508/241 |
| 6,303,548 | B2 |  | 10/2001 | Gao ........................ 508/469 |
| 6,313,077 | B1 |  | 11/2001 | Stunnenberg et al. ....... 508/591 |
| 6,646,174 | B2 |  | 11/2003 | Clarembeau ............... 585/525 |
| 6,703,353 | B1 |  | 3/2004  | Lok et al. ................. 508/110 |
| 6,824,671 | B2 |  | 11/2004 | Goze et al. .................. 208/19 |
| 6,949,688 | B2 |  | 9/2005  | Goze et al. ................. 585/525 |
| 2002/0137636 | A1 | | 9/2002  | Hartley et al. .............. 508/110 |
| 2003/0119682 | A1 | | 6/2003  | Saini et al. ................ 508/167 |
| 2004/0033908 | A1 | | 2/2004  | Deckman et al. |
| 2004/0094453 | A1 | | 5/2004  | Lok et al. .................... 208/19 |
| 2004/0129603 | A1 | | 7/2004  | Fyfe et al. .................... 208/18 |
| 2004/0154957 | A1 | | 8/2004  | Keeney et al. ................ 208/18 |
| 2004/0154958 | A1 | | 8/2004  | Alexander et al. ........... 208/18 |

FOREIGN PATENT DOCUMENTS

WO   WO 99/38938    8/1999
WO   WO 02/092729   11/2002

* cited by examiner

*Primary Examiner*—In Suk Bullock
(74) *Attorney, Agent, or Firm*—Nancy T. Krawczyk; Andrew B. Griffis

(57) ABSTRACT

The invention relates to a method of making a PAO characterized by a low viscosity, low Noack volatility, and excellent cold temperature properties, using a promoter system comprising an alcohol and an ester. The products comprise trimers obtained by fractionating a hydrogenated bottoms product from an oligomerization process using said promoter system.

14 Claims, No Drawings

METHOD OF MAKING LOW VISCOSITY PAO

CROSS REFERENCE TO RELATED APPLICATIONS

This application claims the benefit of Provisional Application No. 60/662,728 filed Mar. 17, 2005, the disclosure of which is incorporated by reference.

FIELD OF THE INVENTION

The invention relates to a method of making a PAO with low viscosity, low Noack volatility, and excellent cold temperature properties, using a promoter system comprising an alcohol and an ester.

BACKGROUND OF THE INVENTION

Poly α-olefins comprise one class of hydrocarbon lubricants which has achieved importance in the lubricating oil market. These materials are typically produced by the polymerization of α-olefins in the presence of a catalyst such as $AlCl_3$, $BF_3$, or $BF_3$ complexes. Exemplary α-olefins for the manufacture of PAO range from 1-octene to 1-dodecene, with 1-decene being a preferred material. Polymers of higher olefins, such as 1-tetradecene, as described in WO 99/38938 and elsewhere, and lower olefins, such as ethylene and propylene including copolymers of ethylene with higher olefins, as described in U.S. Pat. No. 4,956,122 and elsewhere, can also be used. Oligomerization is typically followed by fractionation and by a step of hydrogenation to remove unsaturated moieties in order to obtain the desired product slate. In the course of hydrogenation, the amount of unsaturation is generally reduced by greater than 90%.

PAOs are commonly categorized by the numbers denoting the approximate viscosity, in centistokes (cSt), of the PAO at 100° C. PAO products may be obtained with a wide range of viscosities varying from highly mobile fluids with a nominal viscosity of about 2 cSt at 100° C. to higher molecular weight, viscous materials which have viscosities exceeding 100 cSt at 100° C. Viscosities as used herein are Kinematic Viscosities determined at 100° C. by ASTM D-445, unless otherwise specified. The term "nominal" as used herein means that the number has been rounded to provide a single significant figure.

Processes for the production of PAO lubricants have been the subject of numerous patents, such as U.S. Pat. Nos. 3,149,178; 3,382,291; 3,742,082; 3,780,128; 4,045,507; 4,172,855; and more recently U.S. Pat. Nos. 5,693,598; 6,303,548; 6,313,077; U.S. Applications 2002/0137636; 2003/0119682; 2004/0129603; 2004/0154957;. and 2004/0154958, in addition to other patent documents cited herein. PAOs are included as the subject of numerous textbooks, such as Lubrication Fundamentals, J. G. Wills, Marcel Dekker Inc., (New York, 1980), and Synthetic Lubricants and High-Performance Functional Fluids, 2nd Ed., Rudnick and Shubkin, Marcel Dekker Inc., (New York, 1999).

A major trend in passenger car engine oil usage is the extension of oil drain intervals. Due to tighter engine oil performance, a need exists for low viscosity PAO products with improved physical properties, e.g., evaporation loss as measured by, for instance, Noack volatility, as well as excellent cold weather performance, as measured by, for instance, pour point or Cold Crank Simulator (CCS) test. Noack volatilities are typically determined according to ASTM D5800; pour points are typically determined according to ASTM D97; and CCS is obtained by ASTM D5293.

The properties of a particular grade of PAO are greatly dependent on the α-olefin used to make that product. In general, the higher the carbon number of the α-olefin, the lower the Noack volatility and the higher the pour point of the product. PAO's having a nominal viscosity at 100° C. of 4 cSt are typically made from 1-decene and have a Noack volatility of 13-14% and pour point of <−60° C. PAO's having a nominal viscosity at 100° C. of 6 cSt are typically prepared from 1-decene or a blend of α-olefins and have a Noack volatility of about 7.0% and pour point of about −57° C.

U.S. Pat. No. 5,789,355 relates to SAE Grade 5W and higher multigrade oils including a basestock and a detergent inhibitor package. The basestock is selected from API Groups I and II (or Groups 1 and 2, respectively). The detergent inhibitor package includes an ashless dispersant derived from an ethylene alphaolefin (EAO).

In U.S. Pat No. 6,646,174, a mixture of about 10 to 40 wt. % 1-decene and about 60 to 90 wt. % 1-dodecene and are co-oligomerized in the presence of an alcohol promoter. Preferably 1-decene is added portion-wise during the single oligomerization reactor containing 1-dodecene and a pressurized atmosphere of boron trifluoride. Product is taken overhead and the various cuts are hydrogenated to give the PAO characterized by a kinematic viscosity of from about 4 to about 6 at 100° C., a Noack weight loss of from about 4% to about 9%, a viscosity index of from about 130 to about 145, and a pour point in the range of from about −60° C. to about −50° C.

An improvement on the conventional processes is disclosed in U.S. Pat. No. 6,824,671. A mixture of about 50 to 80 wt. % 1-decene and about 20 to 50 wt. % 1-dodecene are co-oligomerized in two continuous stirred-tank reactors in series using $BF_3$ with an ethanol:ethyl acetate promoter. Monomers and dimers are taken overhead and the bottoms product is hydrogenated to saturate the trimers and higher oligomers to create a 5 cSt PAO. This product is further distilled and the distillation cuts blended to produce a 4 cSt PAO containing mostly trimers and tetramers, and a 6 cSt PAO containing trimers, tetramers, and pentamers. The lubricants thus obtained are characterized by a Noack volatility of about 4% to 12 %, and a pour point of about −40° C. to −65° C. See also U.S. application Ser. No. 10/959544.

U.S. Patent Application 2004/0033908 is directed to fully formulated lubricants comprising PAOs prepared from mixed olefin feed exhibiting superior Noack volatility at low pour points. The PAOs are prepared by a process using an $BF_3$ catalyst in conjunction with a dual promoter comprising alcohol and alkyl acetate, and the products are the result of blending of cuts.

In general, the lower the molecular weight of the alcohol used in the synthesis, the lower the degree of polymerization and the lower the viscosity of the product. Temperature, residence time, pressure and the concentration of the catalysts also affect the degree of polymerization. However, the normal alcohol used is the major factor that affects the degree of polymerization. Conventional processes not only produce trimers but also tetramers and higher oligomers. Unfortunately, large quantities of trimers, which are in great demand, are not produced by prior art methods even with the use of low molecular weight normal alcohol. Moreover, the separation of the trimers made by prior art methods, usually by distillation, produces other PAOs that are not in great demand.

A PAO that is lighter than 4 cSt at 100° C. can also be made, by way of example, blending PAOs that have nominal 100° C. viscosity of about 2 cSt and about 4 cSt, respectively, such as disclosed in U.S. Pat. No. 6,703,353 and U.S. patent application Ser. No. 2004/0094453. However, such a products have relatively high Noack volatility.

A product having a combination of low viscosity, low Noack volatility, and good cold temperature properties is highly desirable. The present inventors have surprisingly discovered a method of producing oligomers, including a high proportion of trimers, characterizable by low viscosity, low Noack volatility, and excellent low temperature fluidity, without the necessity of blending.

SUMMARY OF THE INVENTION

Trimer rich oligomers are produced in high yield by the use of novel polymerization technique that controls the degree of polymerization with the use of an ester. The ester is a component of the promoter system that also contains a $BF_3$ catalyst. The process comprises contacting a feed comprising at least one α-olefin with a catalyst comprising $BF_3$ in the presence of a $BF_3$ promoter comprising an alcohol and an ester formed therefrom, in a continuously stirred reactor, preferably at least two continuously stirred reactors connected in series, under oligomerization conditions. Products lighter than trimers are distilled off after polymerization from the final reactor vessel and the bottoms product is hydrogenated. The hydrogenation product is then distilled to yield a trimer-rich product.

In an embodiment the products are narrow cut (narrow molecular weight distribution), low viscosity, low Noack volatility PAOs.

In another embodiment the bottoms product obtained is used without blending with a second PAO.

In an embodiment, unreacted monomers and promoters are distilled off in a first distillation column, dimers are distilled off in a second distillation column, and the bottoms product sent to a third distillation column, to yield at least one overhead product and at least one bottoms product. In a preferred embodiment, if the dimers are one of the desired products, hydrogenation is performed after removal of the unreacted monomers in a first distillation column, and dimers are then removed in a second distillation column. In a more preferred embodiments, products are obtained from overheads and/or bottoms product in a third distillation column.

It is an object of the invention to provide a low Noack volatility PAO capable of acting as a basestock in an engine oil formulated to meet SAE Grade 0W multigrade requirements.

It is also an object of the invention to provide a method whereby the viscosity of a PAO product can be controlled by the ratio of alcohol to ester, with the higher viscosity achieved by having a higher alcohol:ester ratio.

These and other objects, features, and advantages will become apparent as reference is made to the following detailed description, including examples, comparative data, and the appended claims.

DETAILED DESCRIPTION

According to the invention, the alphaolefin or mixture of alphaolefins is polymerized continuously using $BF_3$ and $BF_3$ promoted with a mixture of an alcohol and an ester in at least one continuously stirred reactor. In a preferred embodiment, a series of at least two continuously stirred tank reactors is used. The reaction mixture from the final reactor is distilled to remove the unreacted monomers, promoters, and dimers, all of which may be recovered and reused in preferred embodiments. The bottoms product is then hydrogenated to saturate oligomers. The final product may then be distilled from the hydrogenated bottoms to produce, in embodiments, different grades of low viscosity PAO.

In an embodiment, the product is a narrow cut (narrow molecular weight), low viscosity, low Noack volatility PAO. As used herein, the term "narrow cut" means narrow molecular weight range. In its most preferred embodiment, for the present invention, narrow cut, low viscosity, low Noack volatility PAOs will comprise a very high percentage of trimers of the at least alphaolefin feed, preferably at least 85 wt. %, more preferably at least 90 wt. %, still more preferably at least 95 wt. %, yet still more preferably at least 99 wt. % trimer. The meaning of the term "narrow molecular weight range" may be understood by one of ordinary skill in the art in view of the foregoing.

The feed comprises at least one α-olefin. The terms "α-olefin" and "alphaolefin" are used interchangeably herein. The alphaolefins may be selected from any one or more of C3 to C21 alphaolefins, preferably C6 to C16 alphaolefins and more preferably at least one species selected from 1-octene, 1-decene, 1-dodecene, and 1-tetradecene. It is preferred that the alphaolefins are linear alphaolefins (LAOs). Mixtures of any of these alphaolefins mentioned may also be used.

In a preferred embodiment, at least two species selected from 1-octene, 1-decene, 1-dodecene, and 1-tetradecene are used in the feed. In another preferred embodiment, the feed comprises greater than or equal to 40 wt. % -decene, or greater than 40 wt. % 1-decene, or greater than or equal to 50 wt. % 1-decene.

In another preferred embodiment, the olefin feed consists essentially of greater than or equal to 40 wt. % 1-decene, or greater than 40 wt. % 1-decene, or greater than or equal to 50 wt. % 1-decene, with the remainder of the olefin feed consisting essentially of one or more of species selected from 1-octene, 1-dodecene, and 1-tetradecene.

In another preferred embodiment the olefin feed consists essentially of 1-decene, in yet another preferred embodiment the olefin feed consists essentially of 1-decene and 1-dodecene, in still another preferred embodiment the olefin feed consists essentially of 1-dodecene and 1-tetradecene, and in yet still another preferred embodiment the feed consists essentially of 1-dodecene.

In an embodiment, the feed comprises 1-decene. In a preferred embodiment, the feed consists essentially of 1-decene and a promoter according to the invention, co-fed into the reactor comprising an oligomerization catalyst, and the product of the process according to the invention comprises a distillation cut characterized by a viscosity of about 3.6 cSt at 100° C.

In another embodiment, the feed consists essentially of 1-decene, 1-dodecene, and promoter according to the invention, co-fed into the reactor comprising an oligomerization catalyst, and the product of the process according to the invention comprises a distillation cut characterized by a viscosity of about 3.9 cSt at 100° C.

In an embodiment, the olefins used in the feed are co-fed into the reactor. In another embodiment, the olefins are fed separately into the reactor.

In addition to the presence of a conventional $BF_3$ oligomerization catalyst, at least two different promoters (or cocatalysts) are also present. According to the present invention, the two different promoters are selected from (i) alcohols and (ii) esters, with at least one alcohol and at least one ester present.

Alcohols useful in the process of the invention are selected from C1-C10 alcohols, more preferably C1-C6 alcohols. They may be straight-chain or branched alcohols. Preferred alcohols are methanol, ethanol, n-propanol, n-butanol, n-pentanol, n-hexanol, and mixtures thereof.

Esters useful in the process of the invention are selected from the reaction product(s) of at least one alcohol and one acid. The alcohols useful to make esters according to the invention are preferably selected from the same alcohols set forth above, although the alcohol used to make the ester for the promoter used in (ii) may be different than the alcohol used as promoter in (i), or it may be the same alcohol. The acid is preferably acetic acid, although it may be any low molecular weight mono-basic carboxylic acid, such as formic acid, propionic acid, and the like.

It will be recognized by one of ordinary skill in the art that in the case where the alcohol in (i) is different than the alcohol used in (ii) that there may be some dissociation of the ester in (ii) so that it may be difficult to say exactly what the species of alcohol(s) and ester(s) are with precision. Furthermore, (i) and/or (ii) may be added separately from each other or added together, and separately or together with one or more of the olefin feed(s). It is preferred that $BF_3$ and acid/ester be added in the feed together with the one or more alphaolefin.

In this process, it is preferred that the ratio of the group (i) cocatalysts to group (ii) cocatalysts (i.e., (i) : (ii)) range from about 0.2:1 to 15:1, with 0.5:1 to 7:1 being preferred.

As to the boron trifluoride, it is preferred that it be introduced into the reactor simultaneously with cocatalysts and olefin feed. In the case of more than one continuously stirred reactor connected in series, it is preferred that BF3, cocatalyst and olefin feed be introduced only to the first reactor, and preferably simultaneously. It is further preferred that the reaction zone(s) contain an excess of boron trifluoride, which is governed by the pressure and partial pressure of the boron trifluoride. In this regard, it is preferred that the boron trifluoride be maintained in the reaction zone at a pressure of about 2 to about 500 psig, preferably about 2 to 50 psig (1 psi=703 kg/m$^2$). Alternatively, the boron trifluoride can be sparged into the reaction mixture, along with other known methods for introducing the boron trifluoride to the reaction zone.

Suitable temperatures for the reaction are also conventional and can vary from about −20° C. to about 90° C., with a range of about 15° to 70° C. being preferred. Appropriate residence times in each reactor, and other further details of processing, are within the skill of the ordinary artisan, in possession of the present disclosure.

In an embodiment, after steady-state conditions are achieved in the final reactor, product from the final or last reactor is sent to a first distillation column, wherein the unreacted monomers and promoters are distilled off. Steady-state conditions may be ascertained by one of ordinary skill in the art in possession of the present disclosure, e.g., when QI (as discussed below) of samples taken from the final reactor does not change. The bottoms product is then sent to a second distillation column where dimers are distilled off. In embodiments, for instance in the case where the dimers are a desired product, the bottoms product is preferably first hydrogenated prior to distillation of the dimers. A useful dimer product may be, for instance, a PAO having a nominal 2 cSt viscosity. In an alternative, dimers are first distilled off and the bottoms product from the second distillation product is then hydrogenated.

The products taken off overhead from this hydrogenated bottoms product, in a third distillation column, preferably will be a narrow cut, meaning a high percentage of trimer. In an embodiment, the product comprises at least 85 wt. % trimer. In another embodiment, the product comprises at least 95 wt. % trimer. In still another embodiment, the product comprises about 99 wt. % trimer and about 1 wt. % tetramer. The actual molecular weight range will depend on the feed.

Thus, with a feed consisting essentially of 1-decene, a preferred product will be a narrow cut having, for instance, 85 wt. % C30 PAO. In the case of a feed consisting essentially of 1-decene and 1-dodecene, a preferred product will be a narrow cut having, for instance, 85 wt. % C30, C32, C34, C36 PAO. The percentages of each specific carbon number can be attenuated by one of ordinary skill in the art in possession of the present disclosure.

The bottoms product from this third distillation column also yields a useful PAO product, e.g., a PAO having a nominal 6 cSt viscosity.

In an embodiment, a particular advantage of the present invention is the surprising discovery that the viscosity can be controlled by the ratio of alcohol to ester, with the higher viscosity achieved by having a higher alcohol:ester ratio. The degree of polymerization may also be attenuated more finely by controlling the concentration of the alcohol and the ester. This is, again, within the skill of the ordinary artisan in possession of the present disclosure.

EXAMPLES

In the following examples the improvement in the selectivity of trimer yield is indicated by the parameter QI, which is the ratio of wt. % trimer to the sum of wt. % of trimers, tetramers and higher oligomers. The results are set forth in Tables 1 and 2. The properties of the narrow cut trimers and the co-products made in the same process are shown in Tables 3 and 4. These are compared to the conventional PAO's that have similar viscosity. The examples are meant to illustrate the present invention, and it will be recognized by one of ordinary skill in the art in possession of the present disclosure that numerous modifications and variations are possible. Therefore, it is to be understood that within the scope of the appended claims, the invention may be practiced otherwise than as specifically described herein.

Example 1 (Comparative)

1-decene was oligomerized in two continuous stirred-tank reactors in series at 18° C. and 5 psig using a feed consisting essentially of olefin, $BF_3$ and $BF_3$ butanol (complex of the catalyst and the alcohol). The free $BF_3$ concentration was 0.1 wt. % (1.8 mmoles/100 parts olefin feed); the weight ratio of $BF_3$ to $BF_3$ alcohol complex in the feed was 0.2:1. Residence times in the primary and secondary reactors were 1.4 hrs and 1 hr, respectively. When the system reached steady-state, a sample was taken from the second reactor and the composition of the crude polymer was determined by gas chromatography (GC). The % conversion and QI, shown in Table 1, were computed from the GC results. The QI obtained was 0.375, meaning that only 37.5% of the mixture of oligomers (trimers and higher) were trimers.

Example 2

As Example 1, except that the promoter system had $BF_3$ butanol and $BF_3$. butyl acetate and the residence times in the primary and secondary reactors were 0.5 hr and 1.3 hrs, respectively. The mole ratio of butanol to butyl acetate was 7 to 1; the weight ratio of free to complexed $BF_3$ is 0.1:1. With the addition of $BF_3$. butyl acetate in the promoter system, the conversion was lower and more trimers were produced as indicated by the higher QI of Example 2 compared to that of Example 1, as shown in Table 1.

Example 3

Same as Example 2, except that the concentration of the $BF_3$. butyl acetate complex was increased so that the promoter system had a $BF_3$. butanol : $BF_3$. butyl acetate ratio of 4:1; the weight ratio of free to complexed $BF_3$ was 0.08:1. With the incorporation of more acetate in the promoter system, conversion is similar to that in Example 2, while the QI of the polymer, also shown in Table 1, is increased to 0.651.

Example 4

Same as Example 2, except that the promoter system had a still further increase in $BF_3$. butyl acetate so that the ratio of $BF_3$-butanol to $BF_3$-butyl acetate was 2.5:1, the reaction temperature was at 21° C., and the residence times in the primary and secondary reactors were 1.7 hrs and 0.7 hr, respectively. Again, as shown in Table 1, the QI increased still further with the simultaneous increase in temperature and acetate content, despite the higher conversion attained.

TABLE 1

1-Decene Feed

| Ex. | Promoter System | Reaction Temperature | Residence Time in Primary/Secondary Reactors (in hours) | % Conversion | QI |
|---|---|---|---|---|---|
| 1 | BF3-Butanol | 18° C. | 1.4/1 | 80 | 0.375 |
| 2 | 7:1 BF3-Butanol/BF3-Butyl acetate | 18° C. | 0.5/1.3 | 76 | 0.575 |
| 3 | 4:1 BF3-Butanol/BF3 Butyl Acetate | 18° C. | 0.5/1.3 | 76 | 0.651 |
| 4 | 2.5:1 BF3-Butanol/BF3-Butyl Acetate | 21° C. | 1.7/0.7 | 90 | 0.733 |

Example 5 (Comparative)

Same as Example 1, except that the feed was a mixture containing 70 wt. % 1-decene and 30 wt. % 1-dodecene, the promoter system was $BF_3$. ethanol e residence times in the primary and secondary reactors were 1.3 hrs and 0.94 hr, respectively. The conversion and QI of the polymer are shown in Table 2. By using a mixture of 1-decene and 1-dodecene and lower molecular weight alcohol than that used in Example 1, the QI increased to 0.51.

Example 6

Same as Example 5, except that a dual promoter system of $BF_3$. ethanol and $BF_3$. ethyl acetate was used, in the ratio of 12:1. The addition of $BF_3$. ethyl acetate to the promoter system resulted in a QI that was higher than that of Example 5, as shown in Table 2, below, even though the conversion of Example 5 was lower.

Example 7

Same as Example 5, except that the promoter system used was 3.5:1 in $BF_3$. butanol : $BF_3$. butyl acetate. The QI still increased even when a higher molecular weight alcohol-alkyl acetate system was used. The conversion, however, was lower.

Example 8

Same as Example 7 except that the olefin feed mixture contained 60 wt. % 1-decene and 40 wt. % 1-dodecene. When the feed mixture contained more 1-dodecene, the QI was reduced even if the conversion was similar to that of Example 7

TABLE 2

1-Decene/1-Dodecene feed

| Ex. | C10/C12 Ratio Wt./Wt. | Promoter System | Reaction Temperature | Residence Time in Primary/Secondary Reactors (in hours) | % Conversion | QI |
|---|---|---|---|---|---|---|
| 5 | 70:30 | BF3-Ethanol | 18° C. | 1.3/0.94 | 88 | 0.51 |
| 6 | 70:30 | 12:1 BF3-Ethanol/BF3 Ethyl Acetate | 18° C. | 1.3/0.94 | 93 | 0.582 |
| 7 | 70:30 | 3.5:1 BF3-Butanol/Butyl Acetate | 18° C. | 1.3/0.94 | 85 | 0.682 |
| 8 | 60:40 | 3.5:1 BF3-Butanol/Butyl Acetate | 18° C. | 1.3/0.94 | 86 | 0.671 |

Example 9 (Comparative)

A low viscosity mixture containing 7.2 wt. % PAO with a nominal viscosity of 2 cSt and 92.8 wt. % of PAO with nominal viscosity of 4 cSt, was made from commercial samples. The properties are shown in Table 3, below. Although the blend's viscosity was low, the Noack volatility was high due to the high dimer content.

Also shown in Table 3 are two references—Reference A (SpectraSyn™ 4 PAO) and Reference B (Synfluid® 4 PAO). These are both commercially-available PAOs from Exxon-Mobil Chemical Company and Chevron Phillips, respectively, with nominal viscosity of 4 cSt. Both references have broad molecular weight distribution as indicated by oligomer distribution.

Example 10

This example used the product obtained in Example 4. In Example 4, a sample was taken from the second reactor when steady-state condition was attained. This sample was distilled to remove the monomer and dimer. The bottoms stream was hydrogenated to saturate the trimer and higher oligomers. The hydrogenated product was distilled and two cuts of PAO were obtained, one (overhead) with a nominal viscosity of 4 cSt, shown as Example 10A in Table 3, below, and one (bottoms product) with a nominal viscosity of 6 cSt, shown as Example 10B in Table 4, further below.

From Example 10A, the PAO that had a nominal viscosity of 4 cSt produced in this process was mostly trimers—greater than 95% trimers. It had a narrow molecular weight distribution and had a 100° C. and −40° C. viscosities that were lower than the references. It also had a good Noack volatility.

The co-product, shown in Table 4, had a nominal viscosity of 6 cSt and better Noack volatility and low temperature viscosity than conventional, commercially available 1-decene-based PAO that has a nominal viscosity of 6 cSt (Reference C, commercially-available, nominal 6 cSt PAO, from ExxonMobil Chemical Company).

Example 11

Same as Example 10, except using the product produced in Example 8 instead of Example 4. The PAO produced that had a nominal viscosity of 4 cSt, shown as Example 11A in Table 3, was also narrow cut and had better low temperature viscosity and Noack volatility than the conventional PAOs that have a nominal viscosity of 4 cSt (References A and. B).

The co-product cut, Example 11B, had a nominal viscosity of 6 cSt and was also superior to both commercially available C10-based and mixed olefin-based (C8/C10/C12) references, C and D, respectively. Reference D is commercially-available, also a nominal 6 cSt PAO, from ExxonMobil Chemical Company.

TABLE 3

Properties of Narrow Cut Trimers (overhead product)

| Ex. | Feed | 100° C. K.V. (cSt) | −40° C. K.V. (cSt) | VI | Noack Volatility (wt. %) | Oligomer Distribution Dimer/Trimer/ Tetramer/ Pentamer (wt. %) |
|---|---|---|---|---|---|---|
| Ref A | C10 | 4.00 | 2728 | 123 | 12.4 | 0.8/77.8/18.3/3.1 |
| Ref B | C10 | 3.81 | 2387 | 122 | 14.2 | 0.8/87/11.6/0.6 |
| 9 | C10 | 3.86 | 2383 | 125 | 17.8 | 7.5/67.8/20.4/4.3 |
| 10A | C10 | 3.62 | 2057 | 121 | 15.5 | 0/95.2/4.8/0 |
| 11A | 60:40 C10:C12 | 3.86 | 2499 | 126 | 11.3 | 0.8/96.7/2.5/0 |

TABLE 4

Properties of Co-Products of Narrow Cut Trimers (bottoms product)

| Ex. | Feed | 100° C. K.V. (cSt) | −40° C. K.V. (cSt) | VI | Noack Volatility (wt. %) |
|---|---|---|---|---|---|
| Ref C | C10 | 5.80 | 7800 | 136 | 7.5 |
| 10B | C10 | 5.86 | 7959 | 137 | 6.6 |
| Ref D | 10:60:30 C8:C10:C12 | 5.86 | 7712 | 138 | 6.6 |
| 11B | 60:40 C10:C12 | 5.90 | 7200 | 143 | 6.0 |

Kinematic Viscosity (K.V.) were measured according to ASTM D445 at the temperature indicated (e.g., 100° C. or −40° C.).

Viscosity Index (VI) was determined according to ASTM D-2270.

Noack volatility was determined according to the ASTM D5800 method, with the exception that the thermometer calibration is performed annually rather than biannually.

Pour point was determined according to ASTM D5950.

Oligomer distribution was determined by using the Hewlett Packard (HP) 5890 Series II Plus GC, equipped with flame ionization detector (FID) and capillary column.

The low viscosity and low volatility PAOs made according to the present invention are useful by themselves as lubricants or functional fluids, or they may be mixed with various conventional additives. They may also be blended with other basestocks, such as API Groups I-III and V, or other conventional PAOs (API Group IV) and also other hydrocarbon fluids, e.g., isoparaffins, normal paraffins, and the like. It has surprisingly been found that PAOs according to the invention may advantageously blended with significant quantities of Group III basestocks into lubricant compositions that meet the property requirements of SAE Grade 0W multigrade engine oil formulations. Group III basestocks by themselves do not have the necessary viscometrics required for 0W30 and 0W40 engine oil formulations. Such formulations are described in commonly-assigned, copending U.S. application Ser. No. 11/338,456.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein.

The invention has been described above with reference to numerous embodiments and specific examples. Many variations will suggest themselves to those skilled in this art in light of the above detailed description. All such obvious variations are within the full intended scope of the appended claims, but particularly preferred embodiments include: a process for the oligomerization of alphaolefins comprising: (a) contacting at least one alphaolefin, an alphaolefin oligomerization catalyst, an alcohol promoter, and an ester promoter in at one continuously stirred reactor under oligomerization conditions for a time sufficient to produce a trimer of said at least one alphaolefin; (b) distilling off unreacted alphaolefin and dimers of said alphaolefin to obtain a bottoms product comprising said trimer; (c) hydrogenating said bottoms product to obtain a hydrogenated bottoms product; and then (d) fractionating said bottoms product to obtain at least one cut comprising a trimer product, and also a process for producing a PAO comprising contacting at least one alphaolefin, an alphaolefin oligomerization catalyst, an alcohol promoter, and an ester promoter in at one continuously stirred reactor under oligomerization conditions for a time sufficient to produce a trimer of said at least one alphaolefin, the improvement comprising distilling off unreacted monomers and promoters in a first distillation column, taking the bottoms product from said first distillation column and distilling off dimers in a second distillation column, taking the bottoms product from said second distillation column and hydrogenating said product to produce a hydrogenated product, sending said hydrogenated product to a third distillation column, and obtaining at least one product from either the overheads or bottoms of said third distillation column. Either of the foregoing preferred embodiment may be further modified and/or characterized by numerous modifications suggested herein, especially said process: wherein said process occurs in at least two continuously stirred reactors connected in series; wherein after said contacting and before a distillation step, said oligomerization conditions occur for a time sufficient to achieve a steady state reaction mixture comprising said trimer; wherein at least one distillation cut comprises a trimer product having a viscosity of less than 6 cSt; wherein after distillation of the monomers, dimers, and promoters, the bottoms product is fractionated to obtain at least two cuts comprising said trimer, one cut having a viscosity of less than 4 cSt and another cut having a viscosity of between about 4 cSt and less than 10 cSt; wherein said trimer product having a viscosity of less than 4 cSt comprises 85 wt. % or greater of trimer; wherein said trimer product having a viscosity of less than 4 cSt comprises 90 wt. % or greater of trimer; wherein said trimer product having a viscosity of less than 4 cSt comprises 95 wt. % or greater of trimer; wherein said trimer product having a viscosity of less than 4 cSt consists essentially of about 99 wt. % trimer and about 1 wt. % tetramer; wherein said contacting further comprises contacting a mixture of alphaolefins comprising more than 40 wt. % 1-decene and greater than 1 wt. % to less than 60 wt. % 1-dodecene; wherein said contacting further comprises contacting a mixture of greater than or equal to 50 wt. % 1-decene and a mixture of greater then 1 wt. % to less than or equal to 50 wt. % 1-dodecene; wherein said contacting comprises contacting at least one alphaolefin selected from C14 alphaolefins, C16 alphaolefins, and mixtures thereof; wherein said contacting comprises contacting at least one alphaolefin selected from C8, C10, C12, C14, and C16 alphaolefins, and mixtures thereof; wherein said alphaolefin is a linear alphaolefin; wherein said ester is an alkyl acetate ester; and also a composition made by or obtainable by any of the foregoing processes; especially a product comprising at least 85 wt. % trimers of 1-decene and having a viscosity of about 3.6 cSt at 100° C.; a product consisting essentially of 99 wt. % trimers of 1-decene and 1 wt. % tetramers; a product comprising at least 85 wt. % trimers of 1-decene and 1-dodecene and having a viscosity of about 3.9 cSt at 100° C.; and a product consisting essentially of trimers of 1-decene and 1-dodecene. Also a preferred embodiment is the use of any of the foregoing or combinations of the foregoing (as would be recognized by one of ordinary skill in the art in possession of this disclosure) in lubricant compositions and other functional fluids, such as hydraulic fluids, diluents, and the like.

What is claimed is:

1. A process for the oligomerization of alphaolefins comprising:
    (a) contacting an alphaolefin feedstock, the feedstock being selected from the group consisting of a) a mixture of alphaolefins selected from C8, C14 or C16 and b) a mixture of 40 wt % or greater of C10 and the remainder selected from C8 or C14, an alphaolefin oligomerization catalyst, an alcohol promoter, and an ester promoter in at least one continuously stirred reactor under oligomerization conditions for a time sufficient to produce a trimer of said at least one alphaolefin;
    (b) distilling off unreacted alphaolefin and dimers of said alphaolefin to obtain a bottoms product comprising said trimer;
    (c) hydrogenating said bottoms product to obtain a hydrogenated bottoms product; and then
    (d) fractionating said bottoms product to obtain at least one cut comprising a trimer product, wherein said trimer product comprises 85 wt % or greater of trimer.

2. The process according to claim 1, wherein said process occurs in at least two continuously stirred reactors connected in series.

3. The process according to claim 1, wherein after step (a) and before step (b), said oligomerization conditions occur for a time sufficient to achieve a steady state reaction mixture comprising said trimer.

4. The process according to claim 1, wherein said at least one cut comprises a trimer product having a viscosity of less than 6 cSt.

5. The process according to claim 1, wherein step (d) comprises fractionating said bottoms product to obtain at least two cuts comprising said trimer, one cut having a viscosity of less than 4 cSt and another cut having a viscosity of between about 4 cSt and less than 10 cSt.

6. The process according to claim 1, wherein said trimer product having a viscosity of less than 4 cSt comprises 85 wt. % or greater of trimer.

7. The process according to claim 1, wherein said trimer product having a viscosity of less than 4 cSt comprises 90 wt. % or greater of trimer.

8. The process according to claim 1, wherein said trimer product having a viscosity of less than 4 cSt comprises 95 wt. % or greater of trimer.

9. The process according to claim 1, wherein said trimer product having a viscosity of less than 4 cSt consists essentially of about 99 wt. % trimer and about 1 wt. % tetramer.

10. The process according to claim 1, wherein said alphaolefin is a linear alphaolefin.

11. The process according to claim 1, wherein said ester is an alkyl acetate ester.

12. In a process for producing a PAO comprising contacting an alphaolefin feedstock, the feedstock being selected from the group consisting of a) a mixture of alphaolefins selected from C8, C14 or C16 and b) a mixture of 40 wt % or greater of C10 and the remainder selected from C8 or C14, an alphaolefin oligomerization catalyst, an alcohol promoter, and an ester promoter in at least one continuously stirred reactor under oligomerization conditions for a time sufficient to produce a trimer of said at least one alphaolefin, the improvement comprising distilling off unreacted monomers and promoters in a first distillation column, taking the bottoms product from said first distillation column and distilling off dimers in a second distillation column, taking the bottoms product from said second distillation column and hydrogenating said product to produce a hydrogenated product, sending said hydrogenated product to a third distillation column, and obtaining at least one product comprising at least 85 wt % trimer from either the overheads or bottoms of said third distillation column.

13. The process of claim 1 wherein the trimer product comprises tetramers, and the ratio of trimer to tetramers in the trimer product is at least 19.8 to 1.

14. A process for the oligomerization of alphaolefins comprising:
    (a) contacting an alphaolefin feedstock, the feedstock being selected from the group consisting of a) a mixture of alphaolefins selected from C8, C14 or C16 and b) a mixture of 40 wt % or greater of C10 and the remainder selected from C8 or C14, an alphaolefin oligomerization catalyst, an alcohol promoter, and an ester promoter in at least one continuously stirred reactor under oligomerization conditions for a time sufficient to produce a trimer of said at least one alphaolefin;
    (b) distilling off unreacted alphaolefin and dimers of said alphaolefin to obtain a bottoms product comprising said trimer;
    (c) hydrogenating said bottoms product to obtain a hydrogenated bottoms product; and then
    (d) fractionating said bottoms product to obtain at least one cut comprising a trimer product, wherein said trimer product comprises 95 wt % or greater of trimer.

* * * * *